United States Patent [19]

Scott et al.

[11] 4,224,949
[45] Sep. 30, 1980

[54] METHOD AND ELECTRICAL RESISTANCE PROBE FOR DETECTION OF ESTRUS IN BOVINE

[75] Inventors: Norman R. Scott; Rick Marshall, both of Ithaca, N.Y.

[73] Assignee: Cornell Research Foundation, Inc., Ithaca, N.Y.

[21] Appl. No.: 852,269

[22] Filed: Nov. 17, 1977

[51] Int. Cl.² .............................................. A61B 5/05
[52] U.S. Cl. .................... 128/734; 128/738; 128/642
[58] Field of Search ................... 128/2.1 Z, 2 H, 2 R, 128/738, 734, 642

[56] References Cited

U.S. PATENT DOCUMENTS

| 3,313,293 | 4/1967 | Chesebrough et al. | 128/2.1 E |
| 3,339,542 | 9/1967 | Howell | 128/2 H |

OTHER PUBLICATIONS

"Journal of Dairy Science", vol. 59, May 1976, pp. 982-985.
"Medical and Biology Engineering", vol. 7, pp. 341-343, Pergamon Press, 1969, printed in Great Britain.

Primary Examiner—George J. Marlo
Attorney, Agent, or Firm—Jones, Tullar & Cooper

[57] ABSTRACT

This invention is drawn to a bovine vaginal probe capable of measuring electrical resistance in a bovine vaginal tract with sufficient accuracy to allow detection of changes in electrical resistance indicative of estrus.

The electrodes of the probe are generally axially aligned on the surface of a generally cylindrical support. In the essentially axially parallel electrode configuration, in order to obtain the desired sensitivity where one set of electrodes are employed, the electrodes should be separated from each other by at least 45° and preferably at least about 90°. One preferred essentially axially parallel configuration employs two sets of electrodes, each separated by approximately 90° so that two sets of resistance figures, ventral and dorsal can be obtained.

9 Claims, 25 Drawing Figures

FIG. 1

FIG. 1A $L_1, L_2$ — CIRCUMFERENTIAL DISTANCE BETWEEN ELECTRODES
$t$ — THICKNESS OF MUCUS
$r$ — RADIUS OF PROBE
$\theta$ — ANGLE BETWEEN ELECTRODES

FIG. 2

FIG. 3
SENSITIVITY VS. $\theta$

FIG.11 ELECTRODE LENGTH h (INCHES)
RESISTANCE AS A FUNCTION OF ELECTRODE LENGTH FOR DIFFERENT THICKNESSES OF $10^{-1}$ M NaCl.

FIG.12 ELECTRODE LENGTH h (INCHES)
RESISTANCE AS A FUNCTION OF ELECTRODE LENGTH FOR DIFFERENT THICKNESSES OF 1 M NaCl.

RESISTANCE AS A FUNCTION OF SOLUTION THICKNESS FOR DIFFERENT PROBE LENGTHS AND NaCl.

FIG. 13

RESISTANCE AS A FUNCTION OF ELECTRODE SPACING FOR THE SAME LENGTH OF ELECTRODE AND THICKNESS OF SOLUTION.

FIG. 14

FIG. 15 $\frac{1}{h} \frac{r\theta(2\pi-\theta)}{2\pi 4}$ (1/INCHES)

RESISTANCE AS A FUNCTION OF $\frac{1}{h} \left[\frac{r\theta(2\pi-\theta)}{2\pi 4}\right]$ SHOWING EXPERIMENTAL VALIDATION OF PREDICTION EQUATION.

FIG. 16 $\left(\frac{1}{h}\right)\left[\frac{r\theta(2\pi-\theta)}{2\pi t}\right]$ (1/INCHES)

RESISTANCE AS A FUNCTION OF $\frac{1}{h}\left[\frac{r\theta(2\pi-\theta)}{2\pi 4}\right]$ SHOWING EXPERIMENTAL VALIDATION OF PREDICTION EQUATION.

FIG. 17  RESISTANCE AS A FUNCTION OF $\frac{1}{h}\left[\frac{r\theta(2\pi-\theta)}{2\pi t}\right]$ SHOWING EXPERIMENTAL VALIDATION OF PREDICTION EQUATION.

FIG. 18  RESISTANCE AS A FUNCTION OF $\frac{1}{h}\left[\frac{r\theta(2\pi-\theta)}{2\pi t}\right]$ SHOWING EXPERIMENTAL VALIDATION OF PREDICTION EQUATION.

FIG. 19 $\left(\frac{1}{h}\right)\left[\frac{r\theta(2\pi-\theta)}{2\pi t}\right]$ (1/INCHES)

RESISTANCE AS A FUNCTION OF $\frac{1}{h}\left[\frac{r\theta(2\pi-\theta)}{2\pi 4}\right]$ SHOWING EXPERIMENTAL VALIDATION OF PREDICTION EQUATION.

EXPERIMENT I. MEAN DORSAL AND VENTRAL ER FOR 29 HOLSTEIN HEIFERS.

FIG. 21

EXPERIMENT II. VENTRO-DORSAL MEAN ER AND MILK PROGESTERONE FOR 19 DAIRY COWS.

FIG. 22

EXPERIMENT III. MEAN VENTRAL ER AND MILK PROGESTERONE LEVELS FOR 47 HOLSTEIN COWS (OVERALL)..

METHOD AND ELECTRICAL RESISTANCE PROBE FOR DETECTION OF ESTRUS IN BOVINE

STATE OF THE ART

The detection of estrus in dairy cattle has been a serious problem for the farmer. Failure to detect estrus at the proper time means delayed breeding and long calving intervals, which result in a decreased production of milk and beef. The problem is further complicated by the increase in herd size where one man must observe more cows. In 1976, the New York Dairy Herd Improvement's reports indicated that the average number of breedings per conception for New York State herds was 1.6. These figures underestimate the actual value because the cows sold for reproductive failure are not included. A conservative average for the calving interval was 398 days (not including cows culled because of extended periods of non-pregnancy). Although milk production has increased because of larger herd sizes, the above examples show that maximum efficiency has not been achieved. Better heat detection techniques must be employed in order to reduce the calving interval nearer to the expected optimum of 365 days.

Many reports have been published indicating that there are changes in the concentrations of various ions (sodium chloride being a major one) in the vaginal mucus at the time of estrus, and that these changes should be detectable by measuring the electrical resistance (ER). Although many of the reports recommend various devices to measure ER, none of them have presented a fundamental explanation, either empirically or theoretically, on how the devices "work". This explanation is important to the proper design of the instrument. It must be sensitive enough to detect the change in resistance but also must be designed in accordance with the cow's physiology so as to give accurate measurements.

A ring probe for detection of estrus in cattle has been described by Metzger et al, Zuchthyg., 7 56–61 (1972). The probe comprised ring electrodes in a plane perpendicular to the longitudinal axis of the probe body.

DESCRIPTION OF THE INVENTION

This invention is drawn to a bovine vaginal probe capable of measuring electrical resistance in a bovine vaginal tract with sufficient accuracy to allow detection of changes in electrical resistance indicative of estrus.

The bovine vaginal probe of the invention comprises a non-conductive, generally cylindrical support means having at least two electrodes essentially parallel to each other and generally oriented to the longitudinal axis of the support means, on the surface thereof near and end of said support means adapted for insertion into a bovine vagina, said electrodes being electrically connected to an ohm-meter which supplies an AC voltage to the electrodes. In operation, the probe is inserted into the vaginal tract of a bovine, e.g. a diary cow, and the electrical resistance of the vaginal mucus is measured by the AC ohm-meter. As the resistance of the bovine vaginal mucus fluctuates during the estrus cycle, the cycle can be followed by repeated measurement. This provides a quick and easy method for determining the time of estrus.

BRIEF DESCRIPTION OF THE DRAWINGS

FIG. 1-A is a detailed schematic view of the insertion end of a probe showing electrode placement and wiring.

FIG. 15 is a graph plotting resistance as a function of $$\frac{1}{h}\left[\frac{r\theta(2\pi - \theta)}{2\pi t}\right]$$

showing experimental validation of prediction equation.

FIG. 16 is a graph plotting resistance as a function of $$\frac{1}{h}\left[\frac{r\theta(2\pi - \theta)}{2\pi t}\right]$$

showing experimental validation of prediction equation.

FIG. 17 is a graph plotting resistance as a function of $$\frac{1}{h}\left[\frac{r\theta(2\pi - \theta)}{2\pi t}\right]$$

showing experimental validation of prediction equation.

FIG. 18 is a graph plotting resistance as a function of $$\frac{1}{h}\left[\frac{r\theta(2\pi - \theta)}{2\pi t}\right]$$

showing experimental validation of prediction equation.

FIG. 19 is a graph plotting resistance as a function of $$\frac{1}{h}\left[\frac{r\theta(2\pi - \theta)}{2\pi t}\right]$$

showing experimental validation of prediction equation.

DETAILED DESCRIPTION OF THE INVENTION

Figure 1:
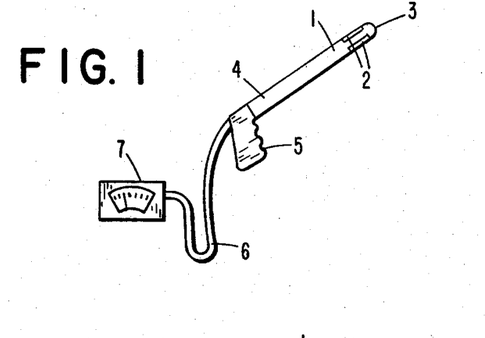
FIG. 1 is a general representation of a probe within the scope of the invention.

With reference to FIG. 1, the bovine vaginal probe of the invention comprises a generally cylindrical support means formed from a physiologically acceptable relatively non-conductive material, i.e. a material havng a D.C. resistivity greater than $10^{10}$ ohm-cm. Many common organic polymeric materials, both thermosetting and thermoplastic are useful as the non-conductive material. Polymethylmethacylate casting resins are particularly suited for use as a support means. The support means is generally cylindrical and the preferred cross-section is circular; however, generally cylindrical shapes such as those having oval cross-sections can be employed so long as the shape conforms to the vaginal tract and provides assured contact of the electrodes mounted thereon with the vaginal walls. Secured to the surface of the support means are one pair of electrodes 2 essentially parallel to each other, and generally oriented to the longitudinal axis of the support means. In the preferred embodiment the electrodes are essentially axially parallel. The electrodes can be of any sufficiently conductive physiologically acceptable material, e.g. metal, preferably stainless steel. The electrode support means 1 has associated therewith an insertion means 4, i.e. an extension which extends beyond the vaginal tract, after proper insertion, to allow insertion into and extraction of the electrode support means from the vaginal tract. As shown in FIG. 1, the extension means has a handle 5 attached thereto for ease of manipulation. While the extension means in FIG. 1 is merely an elongation of the cylindrical electrode support means, the support means need merely be of a length sufficient to carry the electrodes and provide contact of the electrodes with the vaginal walls, and the extension means associated therewith can be of any physiologically acceptable configuration, and formed from a relatively non-conductive material so as not to frustrate the functioning of the electrodes.

Figure 1A:
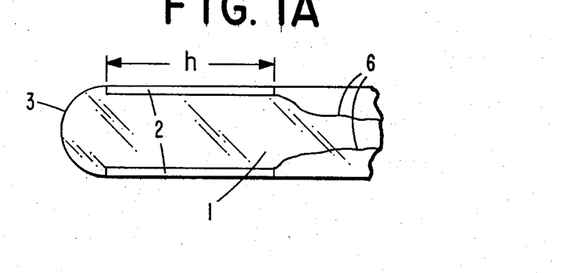

As shown in FIGS. 1 and 1A, the electrodes are electrically connected, e.g. by means of wires, to an Ac ohm-meter which provides an AC current havng a frequency between about 1 KHZ and about 1 MHZ and preferably between about 5 KHZ and about 100 KHZ at a voltage between about 1 vpp and about 10 vpp and preferably between about 3 vpp and about 6 vpp (vpp=volts peak-to-peak).

The electrodes are preferably as narrow as possible consistent with the need for assured reproducible contact with the vaginal mucus, practically the electrodes are usually between about 1/16" and about ½" wide, preferably being between about ⅛" and about ¼" wide. Likewise, the electrodes are preferably as short as possible consistent with the need for assured reproducible contact with the vaginal mucus practically the electrodes are usually between about 1" and 4" long, preferably being between about 2" and about 3½" long.

In the essentially axially parallel electrode configuration, in order to obtain the desired sensitivity where one set of electrodes are employed, the electrodes should be separated from each other by at least 45° and preferably at least about 90°.

The minimum length of the electrode support means is the length of the electrodes; generally the length of the support means is longer than the electrodes to assure, good electrode-mucus contact and consistent electrical measurements.

The diameter of the support means is at least sufficient to assure consistent electrode-mucus contact, the maximum diameter being that physiologically acceptable to the bovine.

Referring again to FIGS. 1 and 1A the insertion end of the probe preferably has a rounded end 3 for ease of insertion.

Figure 7:
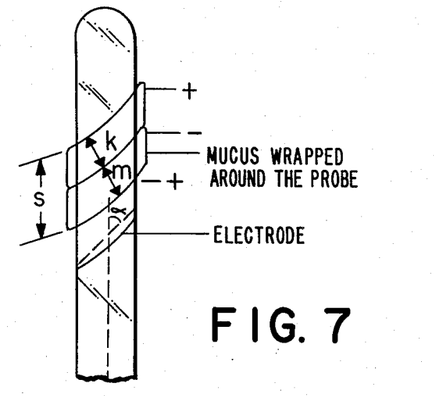
FIG. 7 is a representation of a spiral electrode probe.

While the essentially axially parallel electrode configuration is preferred because of its sensitivity, the electrodes may be secured to the electrode support means in a spiral parallel configuration, where as shown in FIG. 7, the angle of incidence to the longitudinal axis $\alpha$ is 45° or less. The smaller this angle the greater the sensitivity, keeping in mind the separation angles required in the axially parallel configuration. Thus, the terms generally axially aligned and generally aligned with the longitudinal axis of the support means include the positioning of electrodes parallel to or at an angle of less than 45° from the longitudinal axis of the support means.

Figure 20:
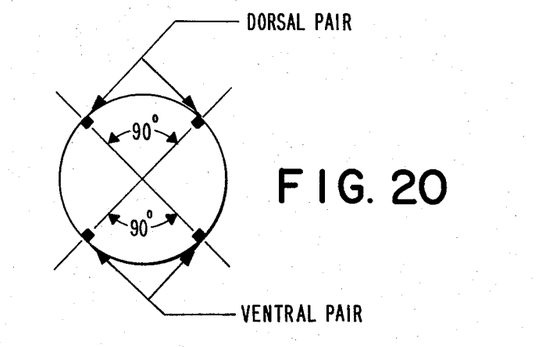
FIG. 20 is a representation of the axially parallel electrode design with four electrodes at 90 degrees.

As shown in FIG. 20, one preferred essentially axially parallel configuration employes two sets of electrodes, each separated by approximately 90° so that two sets of resistance figures, ventral and dorsal, can be obtained.

A convenient manner for constructing a probe in accordance with the invention is to temporarily secure the electrodes, with wires attached, to predetermined positions on the wall of a cylindrical mold. The mold is then filled with a casting resin, e.g. a polymethylmethacrylate casting composition and the composition cured to provide probe with the wires embedded therein and extending from the probe at a predetermined location, usually the end opposite the insertion end of the probe. The resultant probe has the electrodes embedded in the probe, flush with the circumference of the probe, a preferred embodiment.

A number of considerations have been taken into account in the development of the method and probes of the invention, allowing us to arrive at a useful mathematical model. One such consideration is frequency response. Bovine vaginal mucus can be considered an electrolytic solution. Charge is carried through such a solution by the transportation of ions. If an electric field is set up in the solution, the ions will tend to move towards the electrode of the opposite charge. However, there are two major factors which contribute to resist this movement of ions towards the electrodes (Davies, "The Conductivity of Solutions", John Wiley and Sons, Inc., New York (1930) page 30).

First, as an ion rests in solution, an "atmosphere" of the opposite charge is set up around it. This is due simply to the coulombic attraction between charged particles. If an electric field is than applied to the solution, the ions of one charge will move one way but their ionic atmosphere (IA) will tend to move oppositely. The ion must then move against this flow of oppositely charged particles. There is a certain characteristic resistance which the solution will have due to this. However, if the electric field is permitted to stay in one direction (i.e., a DC voltage is applied), the concentration of ions of the same charge, around each electrode, will increase to a certain level. This is referred to as polarization. A region is developed between the electrodes in which there is a lower concentration of ions which results in an increase in resistance.

A second phenomenon which contributes to the resistance of a solution also has to do with the ionic atmosphere. As the ion rests in solution, the IA is set up spherically symmetric about it. But as the ion moves through the solution the IA must increase in strength in the direction of motion and decrease in strength behind it. This causes an asymmetry of the IA which retards the motion of the ion. If the ion was to be suddenly removed, the ionic atmosphere would become random and disappear. The disappearance of the IA, however, takes a finite amount of time and is referred to as the time of relaxation. This time is dependent on both the thickness of the IA and the mobility of the ions. For KCl it is approximately equal to $$\frac{.276(10)^{-10}}{C}$$

sec., where C is the molar concentration of the solution. When an AC voltage is applied across the electrodes the ion will move back and forth in solution. If the frequency of the voltage is small compared to the time of relaxation the symmetry of the charge distribution of the IA will correspond to the instantaneous velocity of the ion. However, at frequencies which are comparable to the time of relaxation, little or no asymmetry will result. Therefore, the resistance of the solution will decrease with increasing frequency.

Employing these two concepts (polarization and asymmetry of the IA), the response of a solution's resistivity for a very broad range of frequencies can be predicted. At a low frequency polarization will occur. As the frequency is increased, polarization will decrease and the resistivity will fall and level off at some characteristic value. This value will then be maintained for quite a wide range of frequencies until the frequency approaches the time of relaxation where it will then decrease.

In designing a probe which would be the most sensitive in detecting the changes in the resistivity of the vaginal mucus, information as to how certain parameters, such as the configuration and size of the electrodes, affect probe sensitivity is essential. Therefore, the probe, as it would operate within the vaginal tract of the cow, was mathematically modeled. By varying the parameters, the most theroetically sensitive probe could then be determined.

When the probe is placed in the vaginal tract of the cow, it is assumed that there exists a thin layer of mucus with thickness t which completely surrounds the electrode end of the probe. As the cow comes in heat, the amount of mucus in the tract increases and the specific electrical resistivity ($\rho$) of the mucus decreases. Therefore, it is desirable to maximize the probe's sensitivity with respect to changes in both t and $\rho$.

Figure 2:
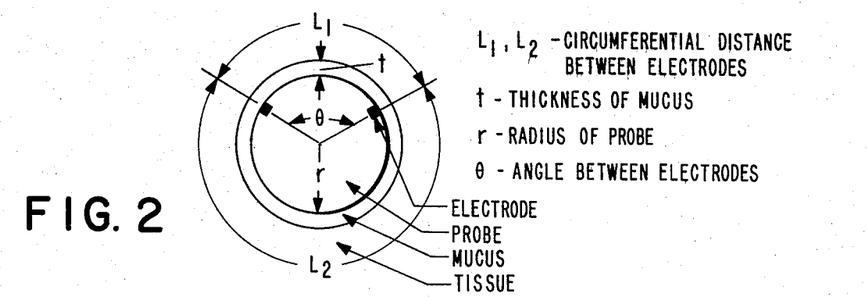
FIG. 2 is a representation of a probe in an idealized vaginal tract of a cow.

Several configurations of electrodes were considered as possible designs for the probe. The first is known as the axially parallel configuration. It consists of thin strips of metal embedded parallel to the axis of the probe. FIG. 2 shows a cross section of such a probe as it would look in the idealized vaginal tract of the cow. The electrodes are h inches long, and assumed to be very narrow (surface area effects will be considered later). They are embedded $\theta$ degrees apart in a probe r inches in radius. Around the probe is the thin layer of mucus in which all of the electric field lines are assumed to be concentrated, as the conductivity of the mucus is much greater than that of the tissue surrounding it.

From FIG. 2 it is seen that the circumferential distance between the electrodes on one side of the probe ($L_1$) would be equal to $\theta r$ where $\theta$ is measured in radians. $L_2$, the distance around the other side, would then equal $(2\pi - \theta)r$. Consider the "slab of mucus $L_1$ inches wide, h long and t thick." Since t is small and all the electric field lines are assumed to be enclosed within the slab, the electric field is considered approximately uniform. Thus, the slab approximates a parallel plate capacitor where the equation $$R = \rho(L/A) \tag{1}$$

applied (Maron and Putton, "Principles of Physical Chemistry" (4th Edition), The MacMillan Company, London, (1965) Page 414). R is the total resistance between the plates, $\rho$ is the specific resistivity of the solution, L is the distance between the plates, and A is the area of the plates. Applying this equation to the upper slab of mucus, $R_1$, the resistance of the slab is given by:

$$R \approx \rho(L_1/th) \tag{2}$$

Likewise, applying it to the lower slab:

$$R_2 \approx \rho(L_2/th) \tag{3}$$

Since these two slabs are connected in a parallel circuit, the total resistivity of the mucus as read by the probe will be $$R = \frac{R_1 R_2}{R_1 + R_2} \simeq \frac{L_1 L_2 \rho}{th(L_1 + L_2)} . \tag{4}$$

Substituting in $r\theta$ for $L_1$ and $(2\pi - \theta)r$ for $L_2$:

$$R \simeq \frac{\rho r \theta (2\pi - \theta)}{2\pi \, th} \tag{5}$$

This equation shows the effects that t, h, r, $\rho$ and $\theta$ have on the resistance which the meter would register for this particular configuration of electrodes. The sensitivity of the probe to changes in $\rho$ and t in the cow is given by $\partial R/\partial \rho$ and $\partial R/\partial t$ :

$$\frac{\partial R}{\partial \rho} = \frac{r\theta(2\pi - \theta)}{2\pi \, th} \tag{6}$$

$$\frac{\partial R}{\partial t} = \frac{\rho r \theta (2\pi - \theta)}{2\pi t^2 h} \tag{7}$$

From Equation (6) it is seen that the sensitivity of the probe to changes in the conductivity of the mucus is directly proportional to r and inversely proportional to t and h. This would mean, therefore, that the probe should be designed with the maximum radius (as would comfortably fit the vaginal tract), the shortest electrodes possible (the electrodes will need to have some length in order to insure good contact with the mucus). The thickness of the mucus (t) depends on the radius of the probe and the physiological make up of the cow. An increased probe radius will probably decrease t since the mucus will accomodate the larger probe rather than the vaginal wall. Due to the nature of the axially parallel configuration both of these effects are desirable (larger r and small t).

Figure 3:
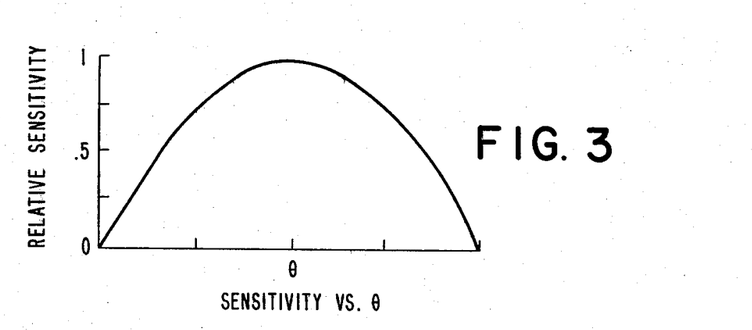
FIG. 3 is a graph plotting probe sensitivity vs the angle between the electrodes.

If the sensitivity of the probe $\partial R/\partial \rho$ is plotted against $\theta$ it can be seen that the relationship is parabolic with the maximum sensitivity obtained at $\theta = \pi$ (see FIG. 3). Therefore, in order to design a probe which would be the most sensitive to changes in the specific resistivity of the mucus the electrodes should be 180° apart.

However, in a probe where the electrodes are 90° apart (four electrodes per probe), one can obtain dorsal and ventral readings from the vaginal tract. Tests show that these two readings may be somewhat different and that an average of the two may be desired in order to detect heat more accurately. The probe, then, can be adapted to give both dorsal and ventral readings and still maintain sensitivity. If the electrodes are set 135° apart, the probe is still within 90% of its maximum sensitivity. This allows room on the probe for two more electrodes. The upper two electrodes can be used for dorsal readings and the lower two for ventral readings.

By comparing Equation 7 with Equation 6 it is seen that $\theta$, r and h all have the same effects on changes in the thickness of the mucus as they did on changes in the specific resistivity. In this case, however, their effects decrease rapidly with increasing thickness (i.e., the design of the probe becomes less crucial with increasing thickness of the surrounding mucus). Therefore, the same design would serve to maximize the sensitivity to both changes in $\rho$ and t.

In the above analysis of the probe the electrodes are assumed to be very thin. However, this may or may not be the optimum design for the probe. For example, one might wish to design the probe with two semicircular plates for electrodes which are separated by only a small distance. Therefore, the effects of the surface area of the electrodes on the probe's sensitivity were considered.

For this particular analysis the thickness of the mucus around the probe is assumed to be very small. To simplify the problem, the effect t has on the total resistivity will not be considered. Instead it will be assumed that all the electric field lines are closely "packed together" along the outer surface of the probe.

Figure 4:
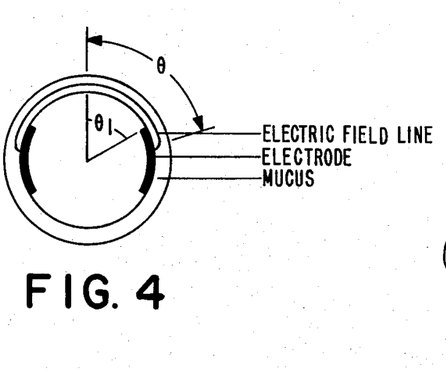
FIG. 4 is a representation of a probe having a finite electrode surface area.

Continuing with the basic model, the theoretical probe will be a rod with electrodes running along it 180° apart but with variable surface area (see FIG. 4). An angle $\theta$ is measured from the vertical running between the two electrode plates. An expression for the resitivity, as the probe would record it, taking into account the effects of the electrode's surface area, will now be developed.

Figure 5:
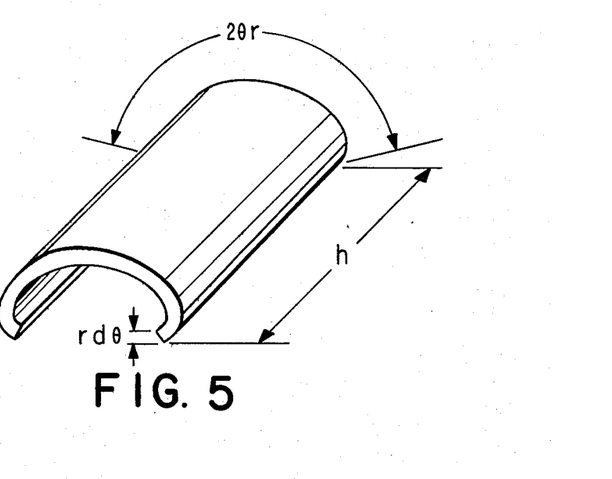
FIG. 5 is a representation of the electric field shell.

Consider a small shell volume with thickness $rd\theta$ and depth h which starts at one electrode and follows the path of the electric field to the other (see FIG. 5). Its circumferential length is approximately $2\theta r$ since its shape approximates that of an arc of a circle (the electric field lines to the right and left of it are enclosed within the small thickness of mucus surrounding the probe).

Because this volume is thin and follows the path of the electric field, it can be assumed that there is a uniform electric field within it. Its resistivity is expressed as:

$$R_s = \rho \frac{L}{A} \approx \frac{\rho \, 2\theta r}{hrd\theta} \tag{8}$$

To simplify the following steps, the solution's conductivity for each shell volume ($C_s$) rather than its resistivity will be calculated:

$$C_s = \frac{1}{\rho} \frac{hd\theta}{2\theta} \tag{9}$$

Since there exist many of these shell volumes laying on top of one another, all connected in a parallel circuit, the conductivity of every small shell volume along the surface of the probe can be summed up to obtain an expression for the total conductivity of the solution as the probe would record it. It is true that since the electric field lines lay on top of one another, the length of each small volume would change according to the thickness of the mucus (the longer shell volumes would be on the outer layer of the mucus). However, since, for the analysis of the surface area, it is assumed that the thickness is small, approximately no changes in lengths will result due to t. Thus, it can be assumed that the length of the shall volume is independent of t.

When $\theta = 90°$, the electric field lines bend around the other side of the probe. Therefore, only the top half of the probe is considered in the equation and then the conductivity is doubled to get:

$$C_t = 2 \int_{\theta_1}^{\pi/2} \frac{hd\theta}{\rho 2\theta} = \frac{h}{\rho} (\ln \frac{\pi}{2} - \ln \theta_1) = \frac{h}{\rho} \ln \frac{\pi}{2\theta_1}$$

where $\theta_1$ is the angle at which the electrode begins.

Converting back to R:

$$R = \frac{\rho}{h \ln (\frac{\pi}{2\theta_1})} \tag{11}$$

Defining the sensitivity of the probe as $\partial R/\partial \rho$, its relationship to h and $\theta_1$ is:

$$\frac{\partial R}{\partial \rho} = \frac{1}{h \ln (\frac{\pi}{2\theta_1})} \tag{12}$$

According to this equation, to maximize the sensitivity of the probe, h should be minimized. Also $\pi/2\theta_1$ should be minimized which can be done by making $\theta_1$ very close to $\pi$ (i.e., make the electrode a very thin wire). Of course, if one makes the electrode too thin, its contact with the mucus may be hindered and invalid readings would be obtained. Therefore, a moderately thin (approximately $\frac{1}{8}''$) electrode might be used.

While the above discussion has been directed to the axially parallel configuration of electrodes, other designs have been suggested and even tried. In light of our ability to theoretically predict the relationship between th solutions resistance and the probe's design parameters, two other configurations were considered.

Figure 6:
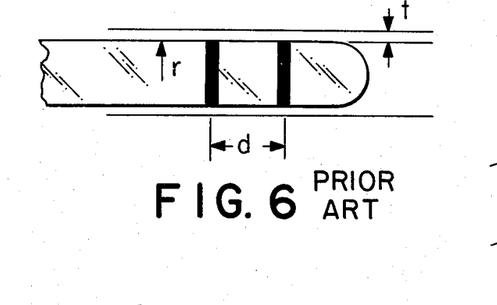
FIG. 6 is a representation of a ring probe in the vaginal tract of a cow.

The first was the prior art ring electrode. As the name suggests, the electrodes are made of two metal rings separated a distance d apart on the shaft of the probe r inches in radius (FIG. 6).

Consider the volume of mucus around the probe where the electric field passes through. It is d inches long and t inches thick. Again the electrodes are assumed to be very thin so d may be an exact distance. If d is fairly large with respect to t, the electric field can be said to be fairly uniform through this volume (neglecting end effects). Thus:

$$R = \rho(L/A) \tag{13}$$

where L=d and A=the cross sectional area of the mucus (which is equal to $2\pi rt + \pi t^2$).

Substituting in for L and A:

$$R = \frac{\rho d}{2\pi rt + \pi t^2} \tag{14}$$

and the probe's sensitivity with respect to $\rho$ and t would be:

$$\frac{\partial R}{\partial \rho} = \frac{d}{2\pi rt + \pi t^2} \tag{15}$$

$$\frac{\partial R}{\partial t} = -\frac{(\rho d)(2\pi r + 2\pi t)}{(2\pi rt + \pi t^2)^2} \tag{16}$$

According to Equations 15 and 16, d should clearly be maximized in order to maximize the overall sensitivity of the probe. This might appear to be an improvement over the key configuration since there is essentially no limit as to how large one could make d (except for the length of the vagina). Of course, if d becomes too large, the mucus in the vaginal tract of the cow may not extend between the electrodes and loss of continuity might result.

Equation 15 indicates that r should be minimized. If t is assumed to be very small (powers of t greater than $t^2$ become insignificant), Equation 16 reduces to:

$$\frac{\partial R}{\partial t} = -\rho d \left( \frac{1}{2\pi rt^2} + \frac{1}{2\pi r^2 t} \right) \tag{17}$$

which would also indicate that r should be minimized. This is where the problem with the ring configuration arises. In trying to minimize r, either contact with the mucus of the vaginal tract would be lost (resulting in random resistance readings) or t would effectively be increased (which would also lower the probe's sensitivity). In the axially parallel configuration, however, r was to be maximized (along with t being maximized). This situation is more desirable in relation to the cow's physiology and therefore the axially parallel configuration becomes a better overall design.

Another possible configuration of electrodes is the "spiral" configuration where the two electrodes are wound around the probe shaft in a double helix fashion (FIG. 7). This design tends to average out the differences between dorsal and ventral readings as well as between anterior and posterior readings.

To develop the equation for the resistance of this configuration, consider two slabs of mucus wrapped continuously down the probe between the electrodes (FIG. 7). The first has width k and goes from the (+) to the (−) electrode. Its resistance is $R_1$. The second slab has width m and goes from the (−) to the (+) electrode. Its resistance is $R_2$. The sum of the two widths is equal to d, the perpendicular distance from the (+) electrode to the (+) electrode after one revolution around the rod. Both slabs have thickness t and length s (the arc length of the spiral).

Thus:

$$R_1 = \rho(k/st) \tag{18}$$

$$R_2 = \rho(m/st) \tag{19}$$

Thus, the total resistance, R, would be:

$$R = \frac{R_1 R_2}{R_1 + R_2} = \frac{\rho \, mk}{st(m + k)} \tag{20}$$

Thus:

$$\frac{\partial R}{\partial \rho} = \frac{mk}{st(m + k)} \tag{21}$$

$$\frac{\partial R}{\partial T} = \frac{\rho \, mk}{st^2(m + k)} \tag{22}$$

Plotting $\partial R/\partial \rho$ against m, the probe's sensitivity is found to be greatest when $m = \frac{1}{2}d$ (i.e., the (−) electrode should be exactly between the (+) electrode). Setting m equal to $\frac{1}{2}d$ our equation becomes:

$$(\partial R/\partial \rho) = (d/4st) \tag{23}$$

From this equation it is clear that in order to maximize the sensitivity d must be maximized and s minimized. In order to do this the path of the spiral would have to be a maximum; the limiting case being two straight electrodes running along the length of the rod, 180° apart (i.e., the axially parallel configuration). Another way to minimize s would be to decrease the radius of the probe. Therefore, the spiral configuration would also seem to be inferior to the axially parallel configuration as far as sensitivity is concerned.

To test whether or not the theories developed above were correct, a number of experiments were conducted. The experiments were divided into two categories: frequency response of the solution, and configuration and size of the electrodes.

EXAMPLE 1

Figure 8:
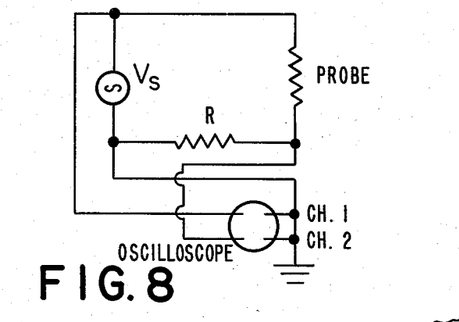
FIG. 8 is a diagram of the circuit for determining frequency effects.
Figure 24:
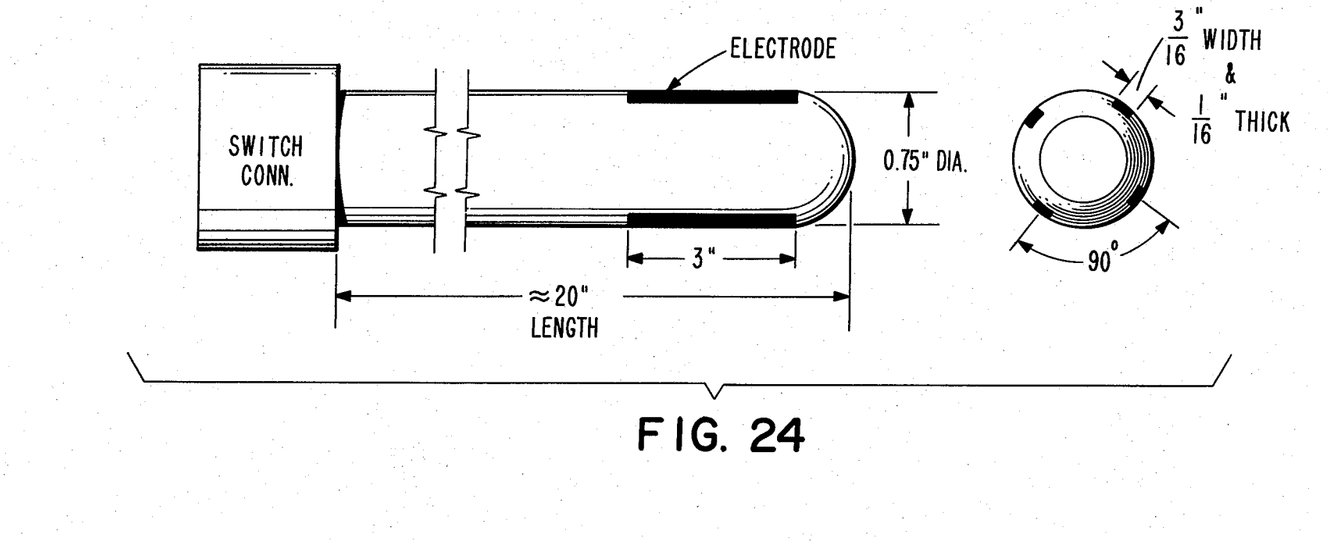
FIG. 24 is a representation of the probe employed in Examples 1 and 3.

To test the hypothesis of the frequency response of the solution, a circuit like that shown in FIG. 8 was used. The probe used in this Example, as well as Example 3, is shown in FIG. 24 and was made from a cast acrylic (Plexiglass) tube (0.75" O.D.; 0.50" I.D.). The electrodes were made from stainless steel (3" long×3/16" wide and 1/16" thick) flush mounted by means of epoxy resin into milled grooves in the tube at the insertion end. Insulated copper wires were soldered to the electrodes and passed through the interior of the tube through the end opposite the insertion end and connected to a switch permitting connection of either electrode pair to the readout instrument. The probe was placed in a salt solution (NaCl) of known concentration. It was then connected in series with a resistor of known resistance (R) and a sinusoidal voltage was applied by a signal generator ($V_s$). By measuring the voltage across the voltage source ($V_s$) and the voltage across the known resistor ($V_r$), the voltage across the electrodes of the probe ($V_p$) was calculated. Then by knowing R and $V_r$, the current (I) through the circuit was calculated. Finally, by dividing $V_p$ by I, the resistance of the solution ($R_p$) between the electrodes was found. The dependence of $R_p$ on frequency could be observed by varying the frequency of the signal generator.

Figure 10:
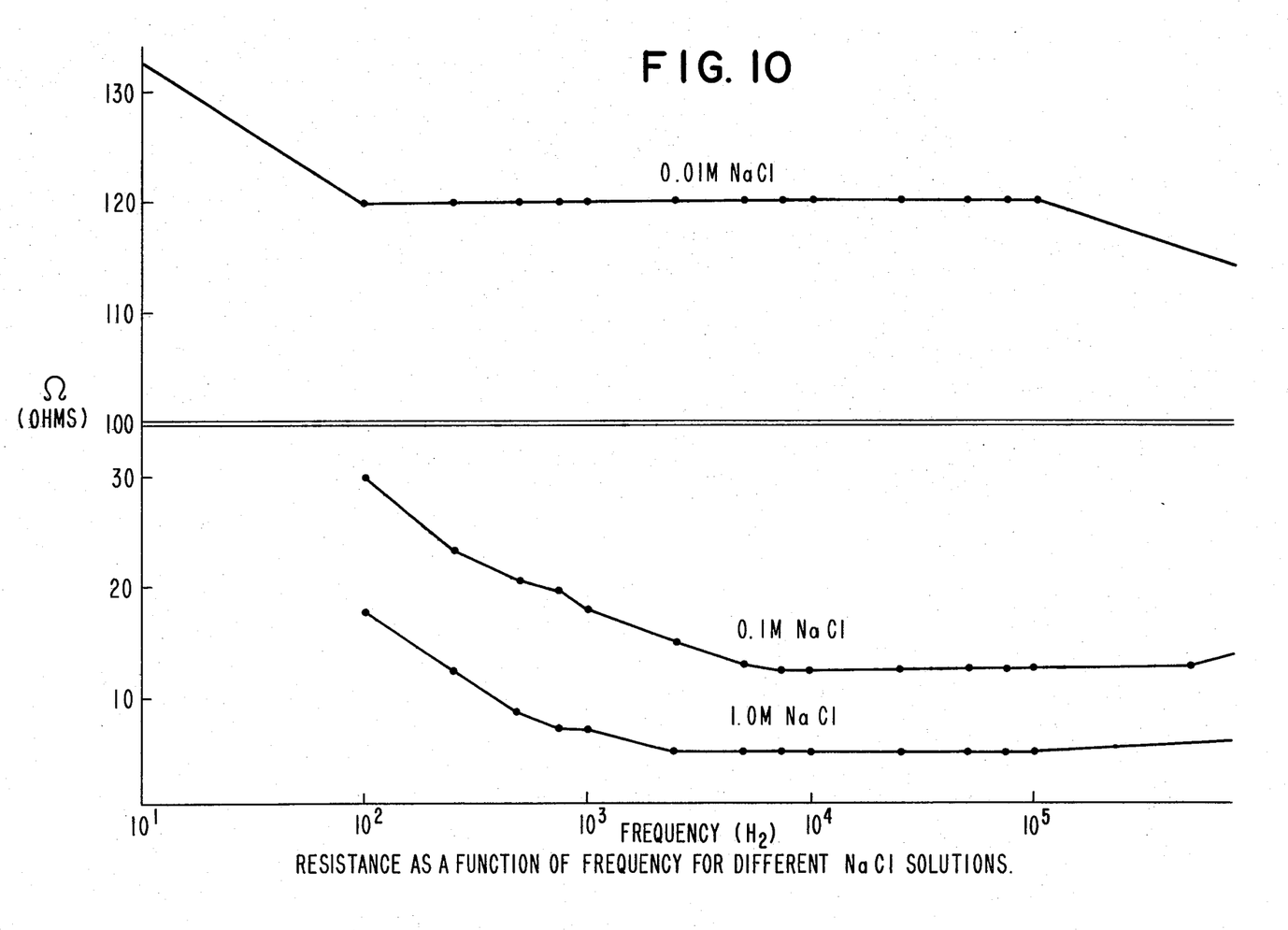
FIG. 10 is a graph plotting resistance as a function of frequency for different NaCl solutions.

FIG. 10 shows the results for various concentrations of solutions. There is, in fact, a plateau region for the probe where the resistance of the solution is independent of the frequency. At a frequency lower than this, the resistance did rise significantly due to polarization as was expected. However, at the highest frequency which the solutions were tested for ($10^6$ Hz) the only solution which showed a significant change in resistance (outside of the error bars of the experiment) was the $10^{-2}$ M NaCl. This could be expected since the time of relaxation is very small and is dependent on the concentration of the ions. Therefore, if $10^6$ Hz was a high enough frequency to effect the resistance of the solutions, the effects would first be seen in the most dilute solution, $10^{-2}$ M. Its resistance did decrease as was expected. For the other two solutions, a higher frequency would have to be used. The frequency of the probe should therefore be set between 5 KHz and 100 KHz in order to minimize the polarization and ionic atmosphere effects, although a frequency as low as about 2.5 KHz is useful. (Of course, as just mentioned, the upper bound to the frequency is still uncertain).

EXAMPLE 2

All of the suggested parameters for the axially parallel probe mentioned above rest on the validity of Equation 5. If this expression for the relationship between resistance and the probe's design parameters is not a correct one, neither is the expression for its sensitivity to changes in $\rho$ and t. Therefore, verification of Equation 5 was sought.

To do this, an apparatus was built in which t, h and $\rho$ could be varied and the resistance as read by the probe recorded. The results could then be compared with the theoretical predictions.

Figure 9:
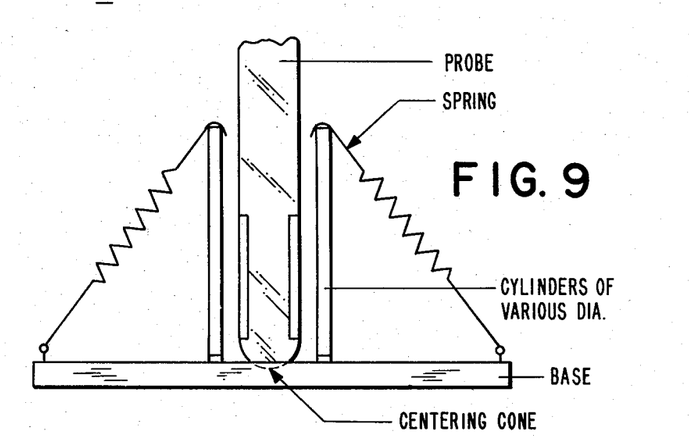
FIG. 9 is a representation of the apparatus used for varying design parameters.

Basically the apparatus consisted of a series of interchangeable plexiglass tubes which could be held down vertically by springs to a plexiglass base (See FIG. 9). The probe was inserted inside one of the tubes; its tip centered by a centering cone and its shaft held parallel to the sides of the tube by three centering screws. A saline solution of NaCl was poured in the space around the probe, $\rho$ was varied by changing the concentration of the saline solution and t was varied by interchanging various diameter tubes. h was varied by filling up the tubes to a certain depth and leaving part of the electrodes exposed. Thus, the only part which would measure resistance would be the part of the electrodes which were submerged. To vary $\theta$, separate probes were constructed in which the electrodes were 45°, 90°, 135° and 180° apart. The radius of the probe was not varied due to limitations on time, but instead held constant.

One test was made using vaginal mucus in the plexiglass test apparatus. Here h was varied and plotted against R for a given t and $\theta$. By doing this, the ER characteristics of the mucus could be compared to those of the saline solution. There was very close agreement between vaginal mucus and the $10^{-1}$ M NaCl with mucus slightly lower in resistance but similar in curve shape.

Figure 11:
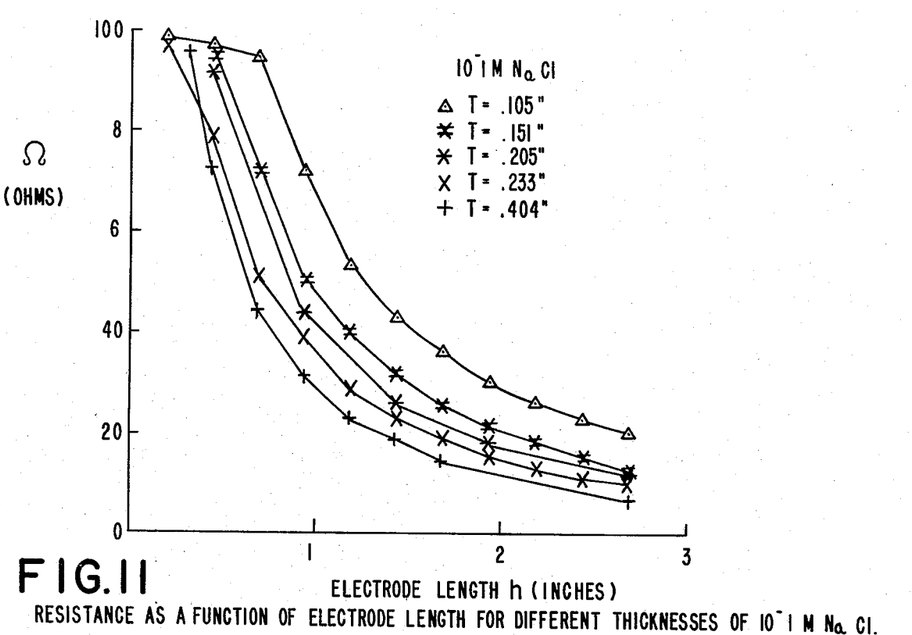
FIG. 11 is a graph plotting resistance as a function of electrode length for different thicknesses of $10^{-1}$ M NaCl.
Figure 12:
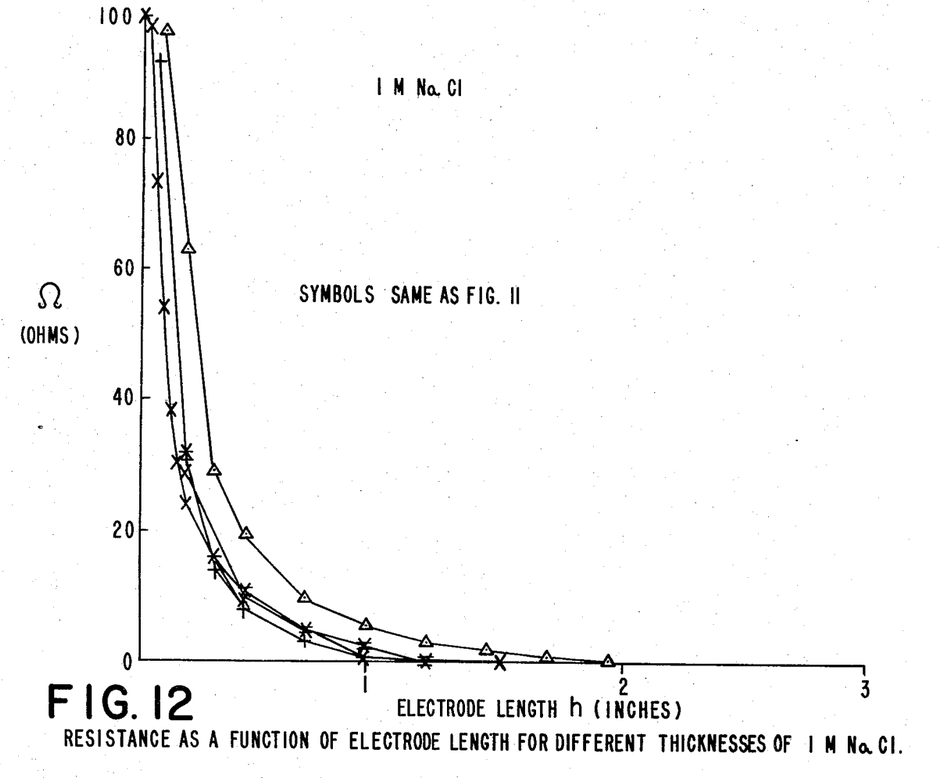
FIG. 12 is a graph plotting resistance as a function of electrode length for different thicknesses of 1 M NaCl.

The experimental results fit very closely to what was expected theoretically for the axially parallel probe. FIGS. 11 and 12 show that the resistance of the solution around the electrodes is in fact inversely proportional to h for both the $10^{-1}$ M and the 1 M NaCl solution. Thus, an expression can be written $R = k_1/h$, where $k_1$ is some constant. By varying t, the value of $k_1$ would be expected to change (since $k_1$ contains t) however, the shape of the curve (1/h) would remain the same. This can also be seen in FIGS. 11 and 12.

Figure 13:
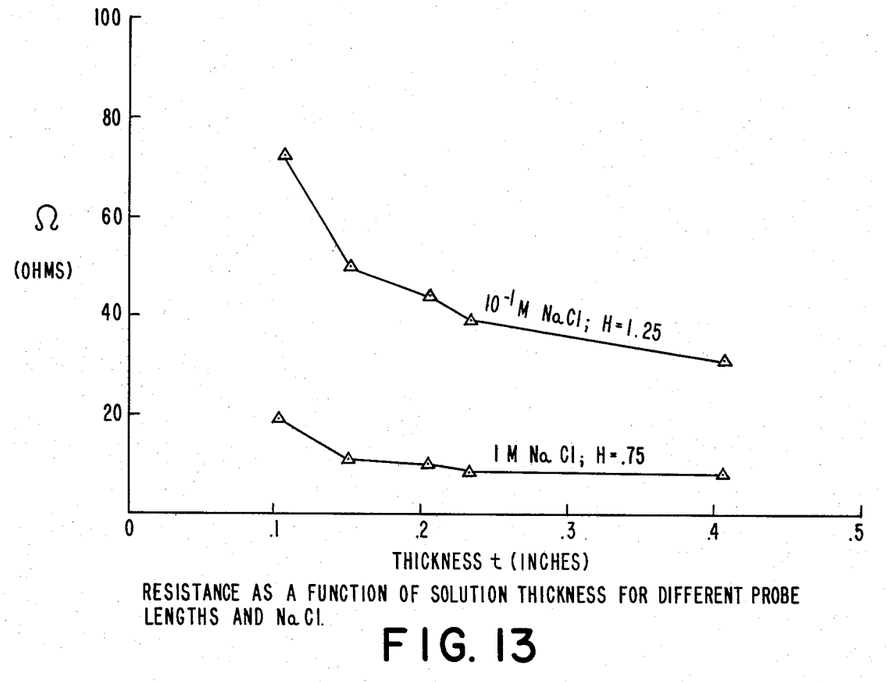
FIG. 13 is a graph plotting resistance as a function of solution thickness for different probe lengths and NaCl.

The resistance also seems to be inversely proportional to t. This is seen in FIG. 13. After t gets thinner than 0.1 inches, problems arise in the support and centering of the probe in the plexiglass tubes. Thus, data could not be obtained for less than 0.1 inches and the full shape of the curve seen. For a more dilute solution t has an effect over a larger range whereas for a more concentrated solution (1 M) the effect of t is rather small beyond 0.15 inches.

Figure 14:
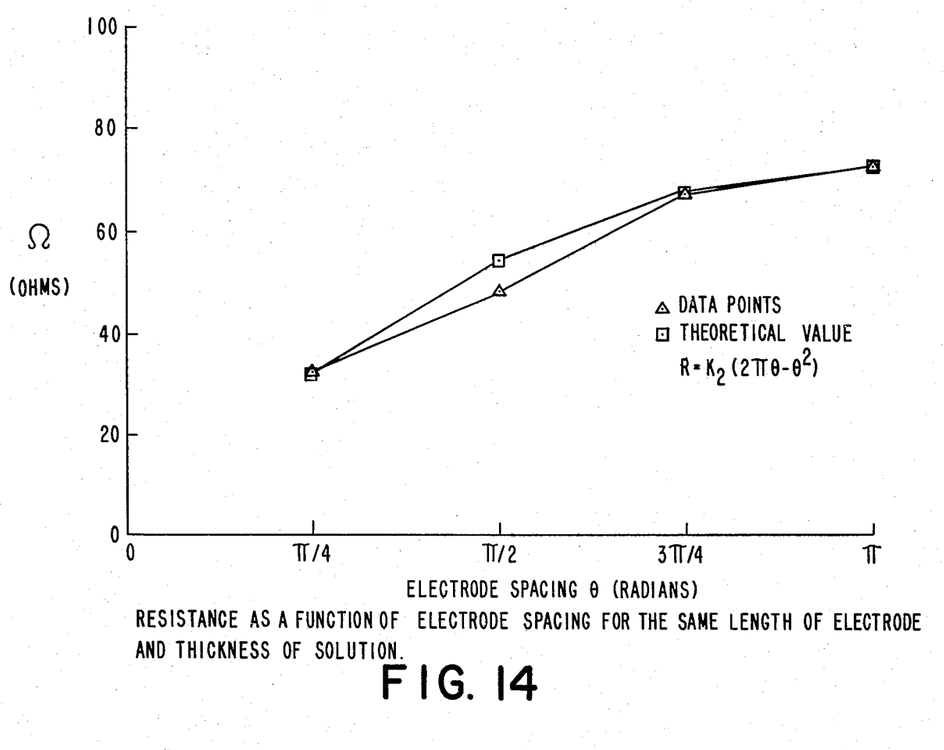
FIG. 14 is a graph plotting resistance as a function of electrode spacing for the same length of electrode and thickness of solution.

When $\theta$ was tested against the resistance, the data fit very closely to the expected curve $R = k_2\theta(2\pi - \theta)$ where $k_2$ is some constant. This is seen in FIG. 14. An appropriate value of $k_2$ was selected and the theoretical expression was plotted along with the data to show the high degree of correlation.

From the above individual results, an expression can be written:

$$R = \frac{k_3 \theta (2\pi - \theta)}{th}$$

where $k_3$ is another constant containing $k_1$ and $k_2$.

This expression which has been experimentally verified is very close to the form of Equation 5. If the two expressions were equal, $k_3$ would equal $\rho r/2\pi$.

The form of Equation 5 can be further checked by graphing R vs.

$$\frac{r\theta(2\pi - \theta)}{2\pi th}.$$

Figure 15:
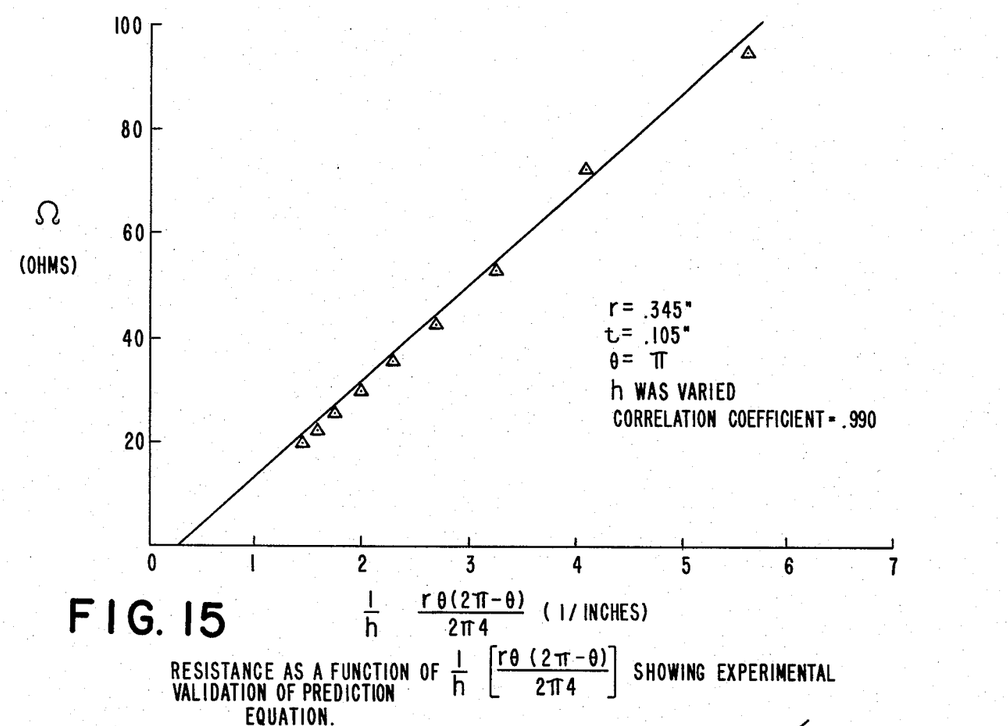
Figure 16:
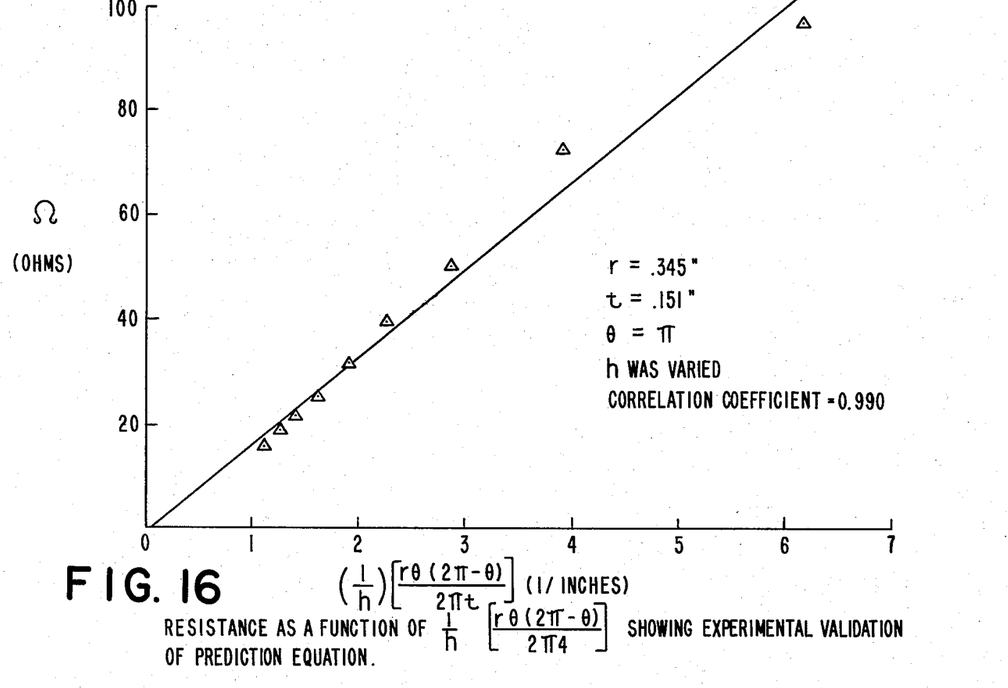
Figure 17:
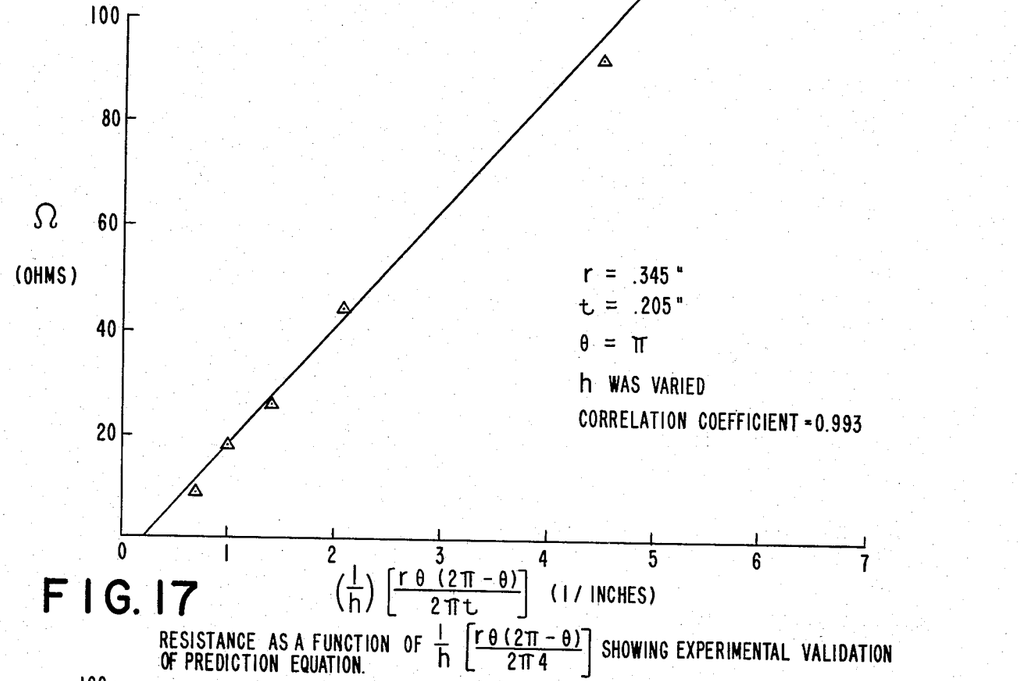
Figure 18:
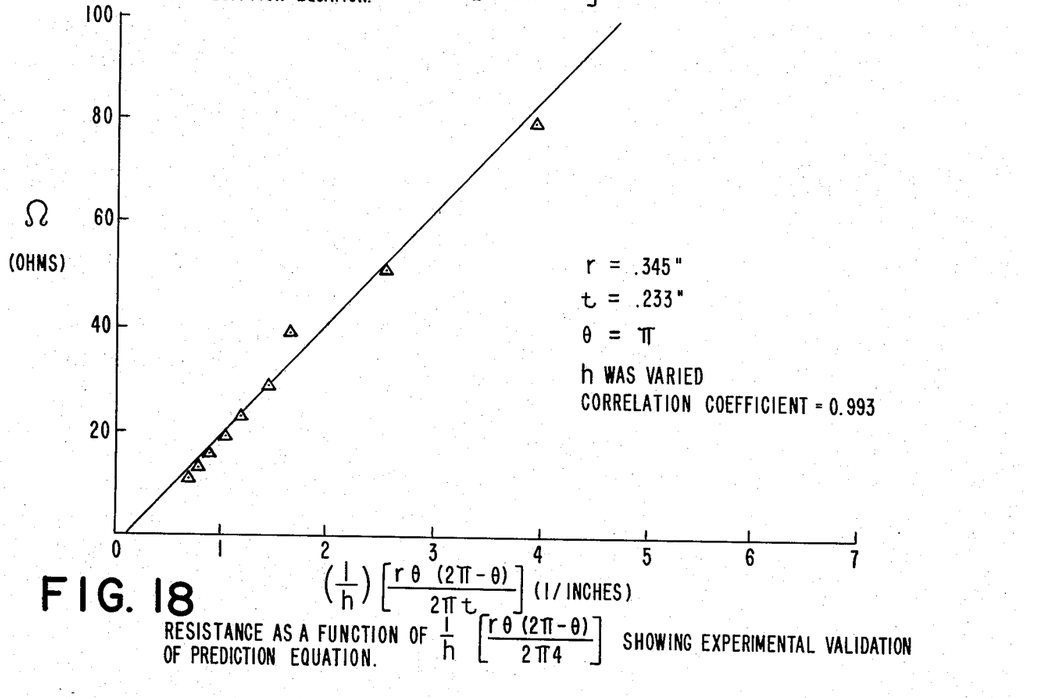
Figure 19:
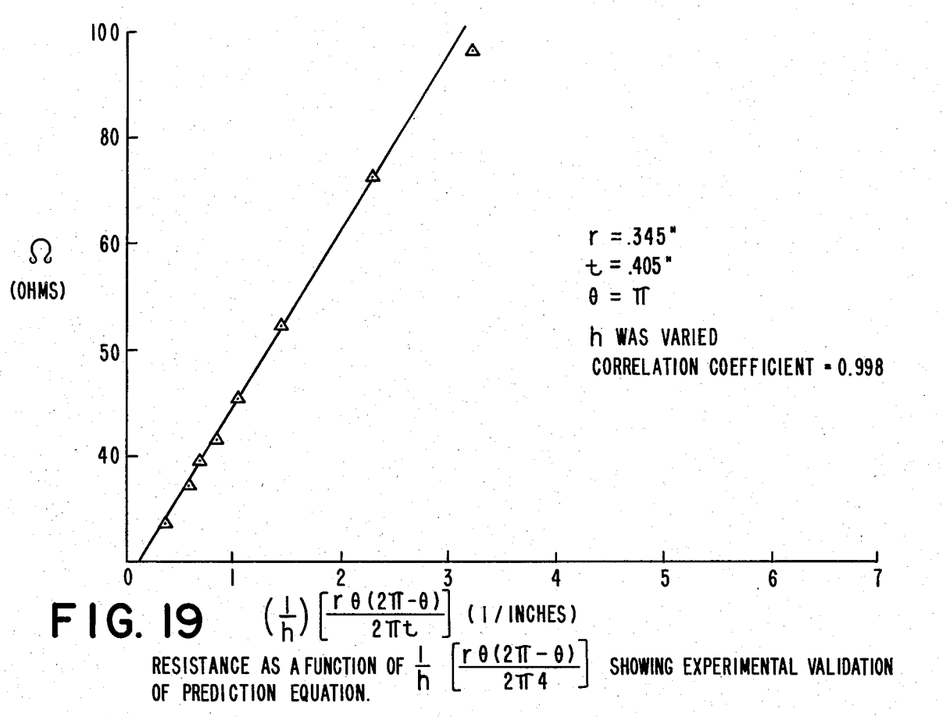

If this is done a straight line with slope of $\rho$ (units being ohm-in) and an intercept of 0 would be obtained. FIGS. 15 and 19 show that there is in fact a linear relationship to a very high degree of correlation (as fitted by the least square method). Each graph shows a fixed value of t, $\theta$, and r as h was varied. If one considers all the points together (where t and h are varied together) a straight line with a correlation coefficient of 0.926 can be fit to the points. The slope of the lines tend to increase as t increases. It is thought that this is due to a spreading of the electric field lines as the thickness of the solution around the probe increases. This would result in an apparent increase in $\rho$ which would in turn lead to a larger slope.

Thus, the effects due to changes in t, h and $\theta$ have been experimentally verified.

When actual bovine mucus was tested in the plexiglass apparatus, curves similar to the expression $R = k_1/h$ were obtained for given $\theta$'s and a given t. This suggests that the mucus behaves similar to an electrolytic solution and thus the equations developed apply.

The above correlations suggest very strongly that Equation 5 is in fact valid if t is small compared to r. Therefore, the design parameters suggested above for the axially parallel probe should, in fact, maximize its sensitivity to the physiological changes in the cow's vaginal tract.

The prior art ring probe was tested in vivo instead of varying its parameters in vitro (Gartland et al, *Journal of Dairy Science*, 59, pp. 982–985 (1976). A definite pattern could be seen in the Electrical Resistance Readings which followed the cycle of the cow, however, variations were too great to establish any firm results. After analyzing the electric field of the ring probe as was done with the axially parallel probe, it seems clear why this is so. There seems to be a conflict between trying to minimize its radius and also maintain contact with the mucus lining of the vagina. For this reason, the design seems to be limited and thus not very hopeful.

The above mathematical model and experiments demonstrate that the frequency of the current supplied to the electrodes should be between about 5 KHz and about 100 KHz; the resistivity of the solution as measured by the axially parallel probe can be expressed as $$R = \frac{\rho r (2\pi - \theta)}{th};$$

the optimal parameter settings of the axially parallel configuration are as follows: (a) $\theta = 180°$ (may be less than this to accomodate 4 electrodes), (b) h should be relatively small ($\sim 2$–$3''$), (c) r should be relatively large ($\sim 0.3$–$0.5''$), (d) electrodes should be moderately thin ($\sim \frac{1}{8}''$); the optimal design of the spiral probe is the axial parallel probe; and that the ring probe contains problems inherent to its design, i.e., the minimization of its radius. It has been shown that bovine mucus appears to have ER characteristics similar to that of a saline solution.

EXAMPLE 3

Three different groups of animals were probed to measure ER of vaginal mucus. The probe as described in Example 1 was operated at a frequency of 2.5 KHz, 3 vpp. These groups were considered as three experiments.

Experiment I.
29 nonpregnant but sexually mature Holstein heifers at Cornell University's Reed Farm.

Experiment II.
24 lactating nonpregnant dairy cows at the New York State College of Agriculture and Life Sciences, Animal Science Teaching and Research Center (ASTARC).

Experiment III.
62 lactating, primarily nonpregnant Holstein cows in Lansing, New York.
  A. Loose Housing
    1. Gordon Cook Farm
    2. David Hardie Farm
  B. Convention (stanchion) Barn
    1. Lawrence Howser Farm Animals in Experiment I were probed for 28 days, in Experiment II for 28 days, and in Experiment III for 40 days. ER was measured by probing on alternate days throughout each experiment. The probe was thoroughly washed with a disinfectant and rinsed at each farm as well as between each animal. The probe was wet with water as a lubricant to facilitate insertion and minimize inflammation. The vulva of each animal was cleaned with a dry paper towel, and the lips of the vulva were widely parted before introducing the probe to prevent carrying organisms and debris into the vagina. The probe was inserted into the anterior portion of the vagina until the os of the cervix was felt. It was then pulled back approximately one centimeter and positioned against the dorsal surface of the anterior vagina. After this ER measurement was taken, the switch connecting the electrodes on the ventral surface of the probe was changed and the ER of the ventral anterior vagina measured. Both measurements were recorded on the individual animal's record form, along with the date.

Milk samples were collected each day the cows were being probed in Experiments II and III. These samples were refrigerated and then frozen in a metanol-dry ice bath, later to be analyzed for milk progesterone levels (by the standard procedure used for milk progesterone, Department of Animal Science, Cornell University).

Visual observations were relied upon for estrus detection in Experiment II. In Experiments I and III, KaMaR, Heatmount Detectors, or a line of "Paintstik" (applied from the tailhead along the midline to the anterior pelvis area), along with visual observations, were used to determine the time of estrus.

RESULTS

Experiment I 24 Heifers

Figure 21:
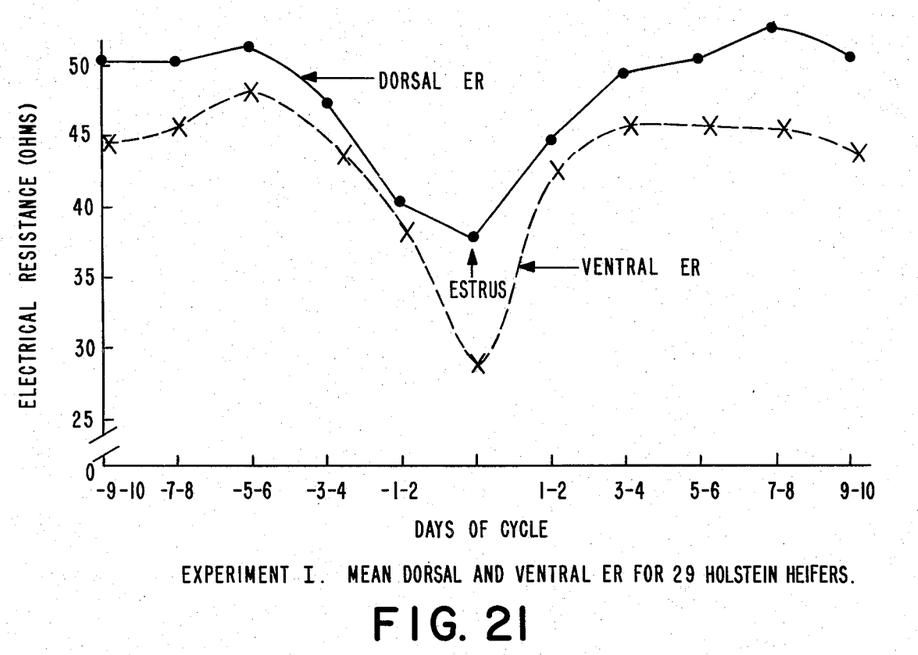
FIG. 21 is a graphic representation of the values measured in Example 3, Experiment I.

The mean ventral and dorsal ER values for Experiment I are illustrated in FIG. 21. The standard errors are not given, but they usually are about ±2.0 ohms. There was individual variations, with 7% of the ventral ER values minimal at some time other than at estrus. The remaining values were lowest at estrus (±1 day). This compared with 85% of the heifers showing a triggered KaMaR or rubbed chalk when visually observed to be in estrus. Generally there were slightly lower ER readings 3–4 days after estrus than at other nonestrus times, which may have been caused by metestrus bleeding. A slight dip at mid-cycle could be due to mid-cycle follicular development known to be present in cattle (and often accompanied by a slight estrogen rise), but not studied in the present experiment.

The dorsal ER readings were not as reliable an indication of estrus, with only 56% having minimal dorsal ER values at estrus (±1 day).

Experiment II ASTARC Lactating Cows

Figure 22:
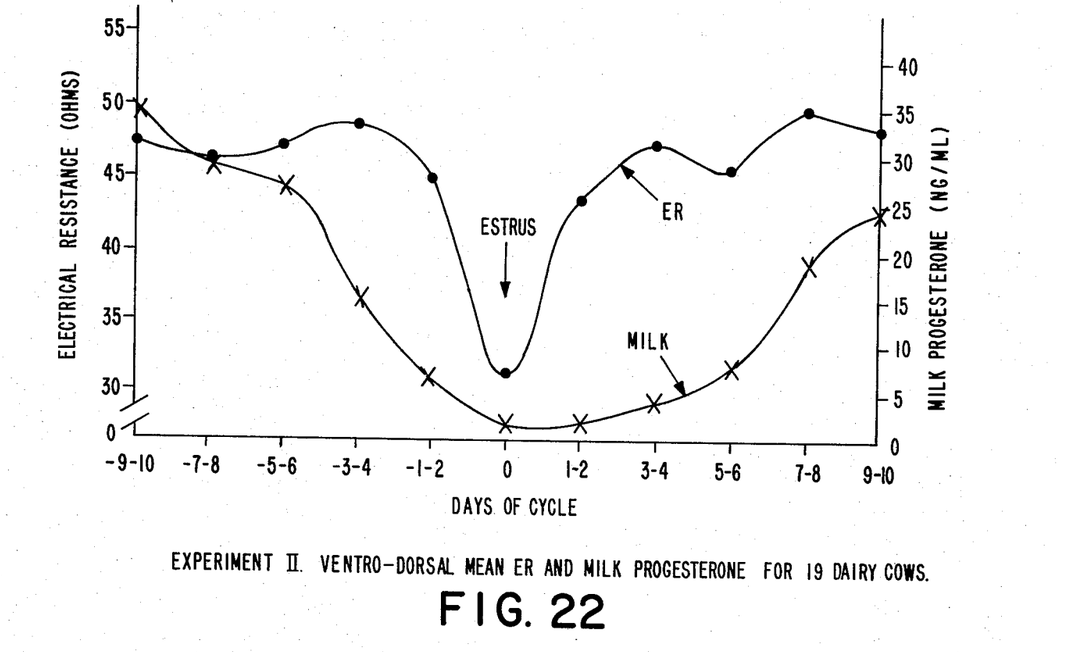
FIG. 22 is a graphic representation of the values measured in Example 3, Experiment II.

The average of the dorsal and ventral ER measurements of mucus and progesterone in milk obtained the same days are illustrated in FIG. 22. Only 19 of the 24 cows studied are included because 5 failed to cycle during the 28 days of experiment. Again, the standard errors were approximately ±2.0 ohms tending to be lower at estrus.

In this experiment the dorsal ER readings were a little more consistent and reliable indicators of estrus. Of all the dorsal ER values, 63% were lowest on the day of estrus. About 90% of the dorsal ER measurements at estrus (Day 0) were $\leq 34$ ohms, while between Days 1–20 9% were $\leq 34$ ohms. Between Days 3–18 93% of the values were $\geq 34$ ohms. Ventral ER measurements followed similar trends, but with a little less consistency. By considering the average of dorsal and ventral ER readings, one obtains 95% of the lowest mean values on the day of estrus (FIG. 22).

Milk progesterone levels change more slowly as the corpus luteum atrophies and a new one forms. The fall in milk progesterone provides some warning of an impending estrus in 2–3 days, but it is not as precise an indicator of the exact day of estrus. Also, it is helpful in determining what sort of endocrine disturbance is present in non-cycling cows. The correlations between milk progesterone levels and the average of central and dorsal ER values were as follows:

| Days of cycle correlated | Correlation coefficient |
|---|---|
| Total cycle | 0.52 |
| Days −4 to +4 | 0.62 |
| Days −6 to 0 | 0.72 |
| Days −4 to 0 | 0.91 |

The highest correlation was obtained for data during the few days preceding and at estrus when both sets of values generally decline considerably.

Six cows cycling on the basis of milk progesterone information were not seen to be in estrus. However, low ER readings were indicative of estrus. These cows were inseminated on the basis of the probe reading and 4 became pregnant as a result.

The 5 cows not cycling had various complications. Two probably had luteal cysts and consistently had high ER values and high milk progesterone levels. Three cows had some infections.

Experiment III 62 Lactating Cows in 3 Herds

Two of the herds were in loose housing and one had conventional stanchions. It was easier to obtain ER readings in the stanchion barns, but once cows were bunched in a corner in loose housing, the measurements were taken quite readily without further restraint. The number of animals finally utilized in this study was as follows:

| Loose housing | Number |
|---|---|
| Total cows | 40 |
| Cycling Cows | 36 (with 57 heats) |
| Non-cycling cows | 4 |
| Stanchion barn | |
| Total cows | 22 |
| Cycling cows | 11 (18 heats) |
| Non-cycling cows | 11 (3 were pregnant) |

Figure 23:
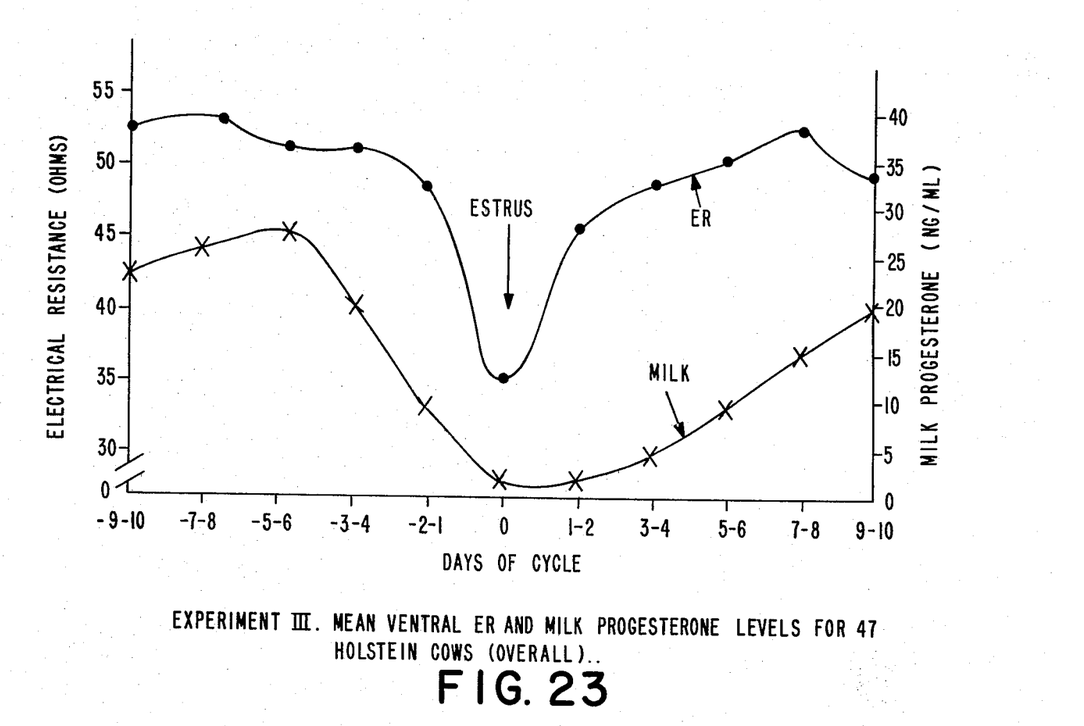
FIG. 23 is a graphic representation of the values measured in Example 3, Experiment III.

Thus there were 47 cycling cows with 75 cycles which were of special interest. The pattern of results (FIG. 23) was similar to Experiment II. On the day of estrus 85% of the ventral ER values and 64% of the dorsal ER values were lowest. While the dorsal value is less reliable as a predictor of the exact day of estrus, it tends to start to decline several days before estrus, and it provides a clue that estrus may be expected within a few days.

Milk progesterone patterns were similar to Experiment II. The values were correlated with ER readings with the following results:

| Position of Probe | Days of cycle | Correlation by housing | | |
|---|---|---|---|---|
| | | Loose | Stanchion | Overall |
| Ventral ER | −6 to 0 | .85 | .82 | .87 |
| | −4 to 0 | .92 | .79 | .92 |
| | −4 to +2 | .88 | .61 | .85 |
| Dorsal ER | −6 to 0 | .87 | .95 | .90 |
| | −4 to +2 | .91 | .99 | .95 |

Pregnancy results were as good for cows inseminated with a low probe reading and not seen in heat as those inseminated at a "reported estrus." However, the number of animals is limited. In cooperation with Eastern A.I. Coop. additional tests in 9 herds were in progress.

From results summarized to date, several conclusions appear to be well substantiated: The rapid decline in ER values at detected estrus or associated with low progesterone and pregnancies achieved upon insemination is a reliable indicator of estrus and ovulation. The probe appears to be at least as accurate as markers on the backs of cows (KaMaRs, chalk). And, cycling cows that are inseminated and maintain a high progesterone level thereafter (indicative of pregnancy) also have high ER readings. Thus a potential pregnancy test at about 21 days exists.

What is claimed is:

1. A bovine vaginal probe for detecting estrus which comprises:
   (a) a relatively non-conductive support means, having a generally cylindrical shape, adapted for insertion into a bovine vaginal tract and contact with the vaginal mucus therein;
   (b) having secured to the surface thereof at least one pair of substantially parallel electrodes aligned parallel to or at an angle of less than 45° from the longitudinal axis of said support means, said electrodes being separated from each other by at least 45°;
   (c) said electrodes being electrically connectable to an AC ohm-meter adapted to determine the electrical resistance of vaginal mucus between said electrodes.

2. The probe of claim 1 electrically connected to said AC ohm-meter.

3. The probe of claim 1 where the electrodes are substantially axially parallel.

4. The probe of claim 3 comprising two sets of electrodes each electrode spaced apart by about 90°.

5. The probe of claim 3 wherein each electrode is between about 1/16 inch and about ⅛ inch wide and between about 1 inch to about 4 inches long.

6. A method of detecting estrus in a bovine which comprises periodically determining the electrical resistance of the bovine vaginal mucus using a bovine vaginal probe which comprises:
   (a) a relatively non-conductive support means, having a generally cylindrical shape, adapted for insertion into a bovine vaginal tract and contact with the vaginal mucus therein;
   (b) having secured to the surface thereof at least one pair of substantially parallel electrodes aligned parallel to or at an angle of less than 45° from the longitudinal axis of said support means, said electrodes being separated from each other by at least 45°;
   (c) said electrodes being electrically connected to an AC ohm-meter adapted to determine the electrical resistance of vaginal mucus between said electrodes, and detecting a change in electrical resistance indicative of estrus.

7. A bovine vaginal probe for detecting estrus which comprises:
   (a) a relatively non-conductive support means, having a generally cylindrical shape, adapted for insertion into a bovine vaginal tract and contact with the vaginal mucus therein;
   (b) having secured to the surface thereof two sets of substantially parallel electrodes substantially axially aligned with the longitudinal axis of said support means, each electrode spaces apart by about 90°, and each electrode being between about 1/16 inch and about ½ inch wide to about 1 inch to about 4 inches long;

(c) said electrodes being electrically connectable to an AC ohm-meter adapted to determine the electrical resistance of vaginal mucus between said electrodes.

8. A method of detecting estrus in a bovine which comprises periodically determining the electrical resistance of the bovine vaginal mucus using a bovine vaginal probe which comprises:

(a) a relatively non-conductive support means, having a generally cylindrical shape, adapted for insertion into a bovine vaginal tract and contact with the vaginal mucus therein;

(b) having secured to the surface thereof at least one pair of substantially parallel electrodes substantially parallel to the longitudinal axis of said support means, said electrodes being separated from each other by at least 45°;

(c) said electrodes being electrically connected to an AC ohm-meter adapted to determine the electrical resistance of vaginal mucus between said electrodes, and detecting a change in electrical resistance indicative of estrus.

9. A method of detecting estrus in a bovine which comprises periodically determining the electrical resistance of the bovine vaginal mucus using a bovine vaginal probe which comprises:

(a) a relatively non-conductive support means, having a generally cylindrical shape, adapted for insertion into a bovine vaginal tract and contact with the vaginal mucus therein;

(b) having secured to the surface thereof two sets of substantially parallel electrodes substantially axially aligned with the longitudinal axis of said support means; each electrode spaced apart by about 90° and each electrode being between about 1/16 inch and about ½ inch wide, and about 1 to about 4 inches long;

(c) said electrodes being electrically connected to an AC ohm-meter adapted to determine the electrical resistance of vaginal mucus between said electrodes, and detecting a change in electrical resistance indicative of estrus.

* * * * *